United States Patent
Yu et al.

(12) 
(10) Patent No.: US 6,399,202 B1
(45) Date of Patent: Jun. 4, 2002

(54) MODIFIED CARBON PRODUCTS USEFUL IN GAS DIFFUSION ELECTRODES

(75) Inventors: Yuan Yu, North Billerica, MA (US); Laurent Kosbach, Puteaux (FR)

(73) Assignee: Cabot Corporation, Boston, MA (US)

( * ) Notice: Subject to any disclaimer, the term of this patent is extended or adjusted under 35 U.S.C. 154(b) by 0 days.

(21) Appl. No.: 09/416,088

(22) Filed: Oct. 12, 1999

(51) Int. Cl.$^7$ .............................. B32B 5/16; H01M 4/02
(52) U.S. Cl. ..................... 428/403; 428/407; 429/29; 429/43; 429/213; 429/217
(58) Field of Search ................ 428/403, 407; 429/29, 43, 217, 213

(56) References Cited

U.S. PATENT DOCUMENTS

| | | | |
|---|---|---|---|
| 4,835,074 A | 5/1989 | Bolster et al. ................ 429/43 |
| 4,877,694 A | * 10/1989 | Solomon et al. .............. 429/27 |
| 4,892,637 A | 1/1990 | Sauer et al. ................ 204/291 |
| 5,116,592 A | 5/1992 | Weinberg .................... 423/415 |
| 5,232,561 A | 8/1993 | Furuya ........................ 204/73 |
| 5,302,274 A | 4/1994 | Tomantschger et al. .... 204/412 |
| 5,312,701 A | * 5/1994 | Khasin et al. ............... 429/42 |
| 5,521,020 A | 5/1996 | Dhar ........................... 429/142 |
| 5,531,883 A | 7/1996 | Cameron et al. .......... 205/626 |
| 5,538,608 A | 7/1996 | Furuya ....................... 204/290 |
| 5,554,739 A | 9/1996 | Belmont ..................... 534/885 |
| 5,561,000 A | 10/1996 | Dirven et al. ................ 429/42 |
| 5,571,311 A | * 11/1996 | Belmont et al. .......... 106/20 R |
| 5,630,868 A | 5/1997 | Belmont et al. ......... 106/31.75 |
| 5,672,198 A | 9/1997 | Belmont .................. 106/20 R |
| 5,698,016 A | 12/1997 | Adams et al. .............. 106/316 |
| 5,707,432 A | 1/1998 | Adams et al. ............. 106/31.6 |
| 5,733,430 A | 3/1998 | Ashida et al. ............. 205/337 |
| 5,783,325 A | * 7/1998 | Cabasso et al. .............. 429/42 |
| 5,837,045 A | 11/1998 | Johnson et al. .......... 106/31.85 |
| 5,846,670 A | 12/1998 | Watanabe et al. .............. 429/42 |
| 5,851,280 A | 12/1998 | Belmont et al. ............. 106/472 |
| 5,986,876 A | 11/1999 | Stepanov et al. ............ 361/502 |
| 6,031,711 A | 2/2000 | Tennent et al. ............. 361/303 |

FOREIGN PATENT DOCUMENTS

| | | |
|---|---|---|
| EP | 0 327 018 | 9/1989 |
| EP | 0 435 835 B1 | 3/1994 |
| JP | 57 208073 A | 12/1982 |
| WO | WO 96/18696 | 6/1996 |
| WO | WO 99/31175 | 6/1999 |
| WO | WO 99/41304 | 8/1999 |

OTHER PUBLICATIONS

"Surface Modification of Carbon Black by Anodic Oxidation and Electrochemical Characterization," Horita et al., Carbon, US, Elsevier Science Publishing, New York, NY, vol. 34, No. 2, 1996, pp. 217–222.

"Oxygen Plasma Processing onto Carbon Black Surface for Gas Diffusion Electrode of Fuel Cell", Horita et al., Chemabs, Chemical Abstracts Service, Columbus, OH, XP–002144593 abstract & TANSO (1994).

International Search Report mailed Aug. 9, 2000 for related International Application No. PCT/US99/30968.

International Search Report mailed Feb. 2, 2001 for related International Application No. PCT/US00/28008.

\* cited by examiner

*Primary Examiner*—Hoa T. Le
(74) *Attorney, Agent, or Firm*—Kilyk & Bowersox P.L.L.C.

(57) ABSTRACT

Gas-diffusion electrodes containing modified carbon products are described wherein the modified carbon product is a carbon product having attached at least one organic group. The modified carbon product can be used for at least one component of the electrodes such as the active layer and/or the blocking layer. Methods to extend the service life of electrodes as well as methods to reduce the amount of fluorine containing compounds are also described.

19 Claims, 3 Drawing Sheets

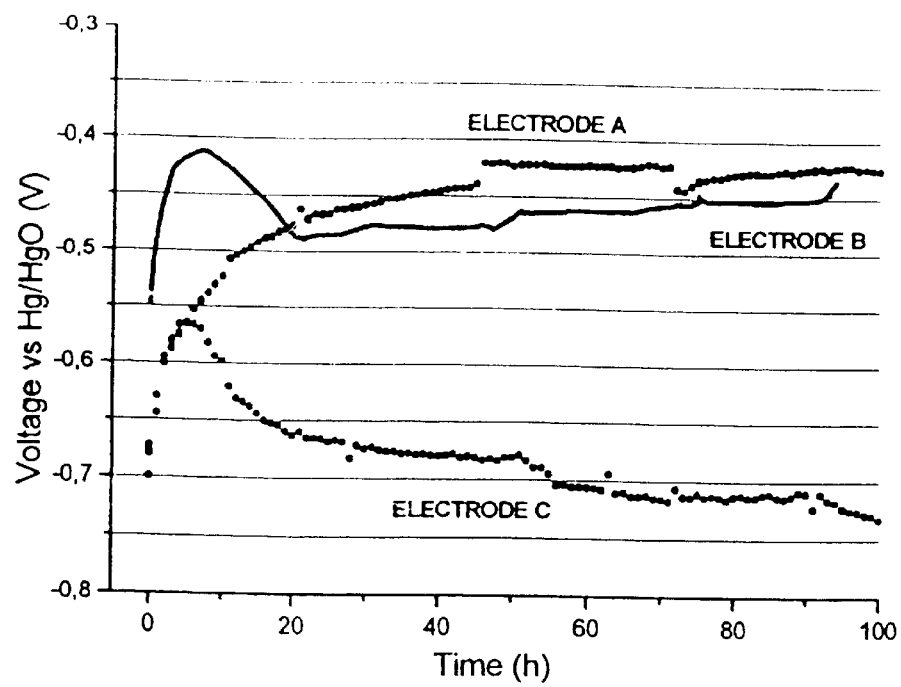
FIG. 1 - Comparison of potential-time curves under constant current load of 200 mA/cm$^2$ and 23 °C: treated Vulcan XC-72R carbon-based electrode (Electrode A); untreated Vulcan XC-72R carbon-based electrode (Electrode B); untreated Shawinigan carbon-based electrode (Electrode C).

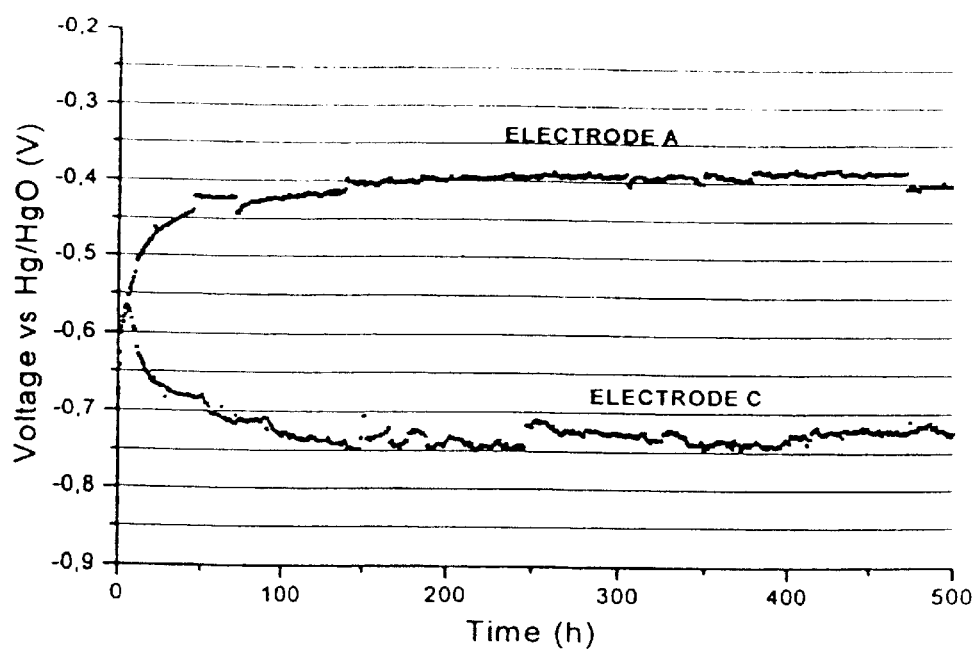
Fig. 2 - Operational curve for the electrrode A under a current load of 200 mA/cm$^2$ and 23°C. Performance curve for the electrode C is also shown for comparison.

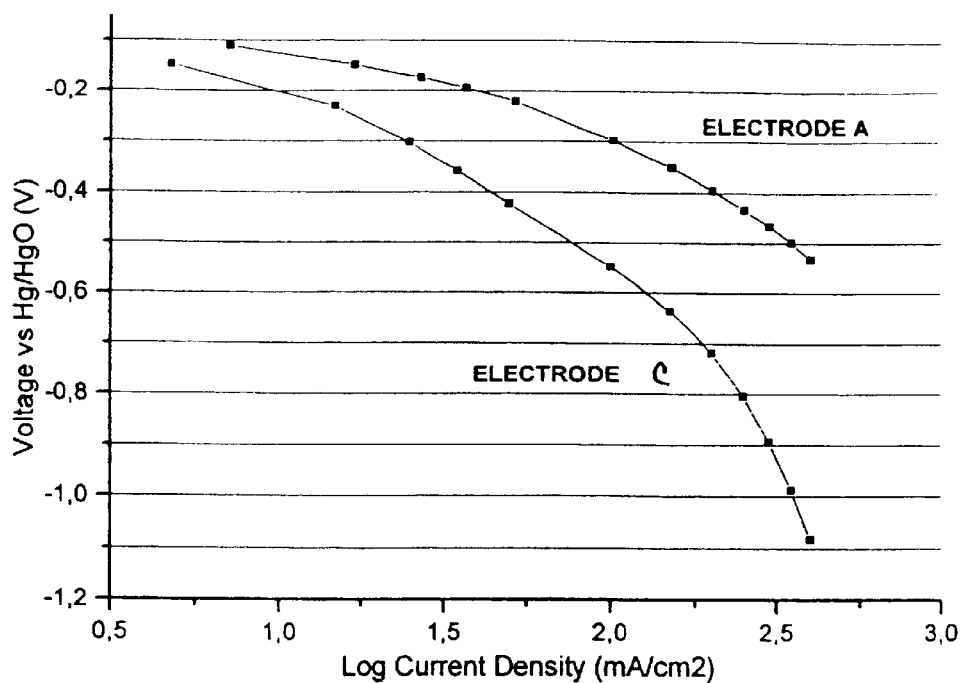
Fig. 3 - Current-potential curves for oxygen reduction in 7.5 M KOH and 23°C on electrodes of types A and C, respectively.

MODIFIED CARBON PRODUCTS USEFUL IN GAS DIFFUSION ELECTRODES

BACKGROUND OF THE INVENTION

The present invention relates to electrodes and the use of gas-diffusion electrodes in a variety of applications. The present invention further relates to methods of preparing gas-diffusion electrodes, including the carbon supports for gas diffusion electrodes. The present invention also relates to carbon products particularly suitable in the manufacture of improved gas-diffusion electrodes, such as air diffusion electrodes.

With respect to gas-diffusion electrode structures, multi-layered composite electrodes are the preferred solution. Depending on the final use of the electrode, two or more layers of carbon blacks combined with fluorine containing compounds are joined into a continuous structure. Double-layered electrodes have a highly hydrophobic carbon support layer coupled to a lesser hydrophobic layer (also known as the active layer) containing catalyzed carbon and suitable binders. A metal screen embedded in the carbon serves as the current collector. The hydrophobic part of the electrode contains a gas feed channel so that the reactant gas can easily diffuse through the pores towards the electroactive layer, where reactions take place. This part of the electrode acts as a barrier to prevent penetration of the electrolyte. Electrolyte in the pores would prevent the diffusion of gas to the reaction layer and this would result in a dramatic deterioration of the electrode's performance. As stated before, the active layer is less hydrophobic than the diffusion layer to ensure partial wetting of the carbon and the electrocatalyst particles. In the active layer, which is also known as the catalyst layer, the reactant gas supplied from the blocking layer diffuses in the gas channels to be dissolved in an electrolyte in contact with carbon or catalyzed carbon so that the electrode reaction is carried out on the carbon or catalyzed carbon in the electrolyte. The structure and the hydrophobic properties of the active layer can be important for efficient electrode operation. It is generally recognised that the major concern in developing an efficient electrode is to improve the wettability of the active layer.

In a three-phase reaction system, such as the active layer, a stable interface between the electrolyte and the gas has to be maintained so that the number of reaction sites remains as high as possible for long operation times. Regarding this point, the ratio of liquid and gas pores in the active layer determines the mass transfer conditions. Poorly wetted pores will result in an acceptably high electrical resistivity and will have low catalyst utilization due to lack of electrolyte, whereas a more hydrophilic interface may flood. Pores with an optimal wettability are filled with only a small film of electrolyte so that the gas diffusion limitations are significantly reduced. The electrolyte quantity in the active layer can be adjusted by a change in the fluoropolymer content in the active layer.

A great variety of wet proofed gas diffusion electrodes exist at the present time which differ in overall structure and configuration. A gas diffusion electrode is generally produced by mixing conductive carbon fine powder and the hydrophobic/hydrophilic fluorine resin powder or suspension thereof, forming the mixture into a sheet, and sintering the sheet.

Water-repellent structures of the diffusion layer are generally achieved by coating the surface of some carbon particles with a hydrophobic material. Polytetrafluoroethylene (PTFE) is one of the most stable and effective hydrophobic agent known. The most popular of the PTFE materials used is in the form of a colloidal suspension, produced by Du Pont de Nemours and Co, Inc. under their Teflon® trademark (Teflon 30-N). The incorporation of PTFE in the blocking layer serves two functions: binding the high surface carbon particles into a cohesive structure and imparting hydrophobicity to the layer.

The most common method to make carbon more hydrophobic is a wet application method. A colloidal aqueous PTFE suspension is blended with carbon powder in an alcohol/water solution to give a mixture containing 5–60 wt. % Teflon®. This mixture is normally produced in the form of an aqueous paste, and it can be rolled, spread, printed, or sprayed onto a substrate, for example a carbon paper. For example, U.S. Pat. No. 5,531,883, incorporated in its entirety by reference herein, relates a method for preparing a hydrophobic support layer by dispersing carbon black in water and adding an aqueous dispersion of PTFE.

U.S. Pat. No. 5,561,000, also incorporated in its entirety by reference herein, relates to a process in which a mixture of carbon and a PTFE suspension is filtered and the filtered-off paste is spread out on a carbon sheet which has been previously soaked in a hydrophobic rendering material such as PTFE in a suspension. The filtered-off paste is applied and pressed in the carbon support by means of a scraping knife. Some cathode structures utilise layers of polytetrafluoroethylene to form protective or backing sheets in order to further increase the hydrophobicity of the carbon black cathodes on the air side.

In the active layer or catalytic layer, a semi-hydrophobic structure is preferred for a more efficient use of the catalyst, and consequently hydrophilic ingredients are used in the air electrode preparation.

The most common method to make carbon partly hydrophilic consists in preparing an alcohol mixture of the carbon powder (with or without catalyst) and a hydrophilic fluorinated resin. One of the most popular hydrophilic fluorinated polymers available on the market is a perfluoric sulphonic acid polymer produced by Du Pont de Nemours and Co, Inc. under their Nafion® trademark (Nafion solution SE-5112). For example, in U.S. Pat. No. 4,877,694, also incorporated in its entirety by reference herein, a mixture of finely powdered active material is prepared by blending catalysed carbon particles together with an alcohol solution of Nafion.® The resulting mixture is dried and finely chopped. An alcohol dispersion of the above product is then filtered on a first prepared backing layer to form a dual phase sheet which is dried and sintered under pressure.

Several further techniques have been developed to increase the catalyst utilization. According to a number of techniques, the catalyst is applied directly on a solid electrolyte membrane and not on the electrode. For example, U.S. Pat. No. 5,561,000 relates to a method for making a gas diffusion layer wherein a catalytic layer is formed on a porous hydrophobic back support in the form of a liquid ink prepared by mixing catalyst particles (20% Pt/C) and a proton conductive monomer solution, such as 5% solution of Nafion®. A non-catalytic intermediate layer containing a mixture of an electron conductive material, such as carbon, and the proton conductive monomer is provided between the support and the catalytic layer. In some cathode structures the solution is made of Pt/C catalyst powder, a Nafion® solution, PTFE in suspension, and carbon black and it is applied directly on a Nafion® membrane.

The problem with these methods is the difficulty in simultaneously obtaining the required porosity and firmness of the layers provided on the support. All the abovementioned patents relate to the use of carbon combined with a colloidal mix, dry mix, or fluorinated polymer solutions. All of the proposed processes involve coating carbon black particles with a fluorinated polymer compound. Although the above-mentioned literature may provide methods which may provide carbon with the proper hydrophobicity/hydrophilicity balance, the methods require elaborate and complex steps or require relatively expensive raw materials.

SUMMARY OF THE INVENTION

A feature of the present invention is to provide carbon products which are useful in gas diffusion electrodes. A further feature of the present invention is to provide gas diffusion electrodes in which the formulation of each single layer is made most suitable for its specific function.

Another feature of the present invention is to provide gas diffusion electrodes with a precisely controlled degree of hydrophobic and/or hydrophilic characteristics by using carbon particles modified with functional groups.

A further feature of the present invention is to provide a method of obtaining carbon supports for gas diffusion electrodes which preferably uses less fluorine containing compounds.

Accordingly, the present invention relates to a modified carbon product. The modified carbon product includes a carbon product having attached at least one hydrophobic organic group and at least one hydrophilic organic group. These modified carbon products are useful in gas diffusion electrodes and can be part of the active layer and/blocking layer or any other component where carbon materials would be useful.

It is to be understood that both the foregoing general description and the following detailed description are exemplary and explanatory only and are intended to provide further explanation of the present invention, as claimed.

BRIEF DESCRIPTION OF THE DRAWINGS

FIGS. 1 through 3 show comparisons of performances between modified carbon-based electrode according to the present invention (electrode A) and untreated carbon-based electrodes (electrodes B and C).

The present invention relates to gas diffusion electrodes, such as the ones used in metal-air batteries, fuel cells, and the like, and also relates to modified carbon products used to form one or more components of the gas diffusion electrodes. In particular, these electrodes have at least one component which contains a modified carbon product. The modified carbon product is a carbon product having attached at least one organic group. The use of a modified carbon product preferably leads to one or more advantages such as longer service life of the electrode and further can permit a decrease in the amount of polymeric binders used and can even permit a decrease or elimination of fluorinated compounds in the electrode which can be quite expensive. Gas-diffusion electrode is a general category which includes air-diffusion electrodes, wherein the air diffusion electrodes can be used in metal-air batteries and fuel cells, and the like. The "gas" in the gas diffusion electrode includes, but is not limited to, air, oxygen, $CO_2$, $H_2$, $NO_2$, and the like.

With respect to the air-diffusion electrode, which is generally used in metal-air batteries and fuel cells, this type of electrode generally is constructed to have a blocking layer and an active layer. The present invention can also be used in gas diffusion electrodes where an active layer is only present or a blocking layer is only present.

In the present invention, the blocking layer, the active layer, or both contain at least one modified carbon product and at least one binder. The blocking layer in the present invention serves the same purpose and function as any other blocking layer in a gas-diffusion electrode. Likewise, the active layer also functions and provides the same purpose as any other active layer in a gas-diffusion electrode.

In more detail, the blocking layer is a layer which separates the air from the electrolyte. The blocking layer however will permit the entry or diffusion of air through the blocking layer in order to contact the electrolyte which enters the active layer in order to promote what is known in the art as the tri-phase or three-phase system. The blocking layer or diffusion layer will typically be hydrophobic in nature in order to prevent the electrolyte which is typically aqueous from escaping through the electrode. The active layer on the other hand has both hydrophobic and hydrophilic qualities because the goal of the active layer is to permit some electrolyte from entering the active layer to wet the carbon material which in part forms the active layer but to also permit air to enter from the diffusion layer to contact the electrolyte in the active layer. Thus, a hydrophilic/hydrophobic balance in the active layer is preferred in order to optimise the operation of the electrode. As mentioned above, if the active layer is overly hydrophilic, then a flooding of the active layer can occur whereas if the active layer is only hydrophobic, then electrolyte will have great difficulty in wetting any of the carbon which in part forms the active layer and thus no interaction will occur between the air and the electrolyte in the active layer.

In the embodiment of the present invention, the blocking layer, the active layer, or both contain at least one modified carbon product. In forming the blocking layer or the active layer, typically the modified carbon product will be combined with at least one binder to form a paste which will then be used to form a layer. The paste which forms the layer is typically put on a conductive substrate such as a nickel substrate or other conductive metal substrate or material. While the blocking layer and/or the active layer can contain any type of modified carbon product, when a modified carbon product forms the blocking layer, it is preferred that the modified carbon product be hydrophobic in nature. Thus, it is preferred that the modified carbon product comprise at least one carbon product having attached at least one organic group which is hydrophobic in nature. In other words, it is preferred that a hydrophobic organic group be attached to the carbon product to form the modified carbon product.

Examples of hydrophobic organic groups which are attached to the carbon product is include, but are not limited to, 1) saturated and un-saturated alkyl groups, aryl groups, ethers, poly ethers, 2) fluorinated saturated and un-saturated alkyl groups, aryl groups, ethers, poly ethers; 3) poly or oligo fluorinated compounds, and the like.

Preferably, the organic group which is attached to the carbon product to promote the hydrophobic properties has the general formula —A—R, wherein A is an aromatic group and/or an alkyl group and R represents fluorine and/or a fluorine containing substituent. The alkyl group is preferably is a $C_1$–$C_{12}$ alkyl group. The aromatic group can include multiple rings. Also, more than one R group can be located on the aromatic group and each of these R groups can be the same or different. More preferably, the hydrophobic group is Ar—$CF_3$ where —$CF_3$ is preferably in the meta position.

With respect to the active layer, as stated earlier, preferably the active layer contains a modified carbon product which promotes hydrophilic and hydrophobic characteristics. In order to promote the hydrophilic characteristics of the carbon product which has a tendency to be naturally hydrophobic, the carbon product preferably has attached at least one type of hydrophilic organic group which can be an aromatic or alkyl group substituted with an ionic group, an ionizable group; a non-ionic hydrophilic group; or a mixture thereof. Preferably, the hydrophilic type organic group is a sulfophenyl group or a carboxyphenyl group, or salts thereof. Examples of the ionic or ionizable group include, but are not limited to, sulfonilic acid groups and salts thereof. Alternatively, the carbon product can have attached at least one type of hydrophobic organic group and can be used in forming the active layer.

In more detail, ionizable functional groups forming anions include, for example, acidic groups or salts of acidic groups. The organic groups, therefore, include groups derived from organic acids. Preferably, when the organic group contains an ionizable group forming an anion, such an organic group has a) an aromatic group or a $C_1$–$C_{12}$ alkyl group and b) at least one acidic group having a pKa of less than 11, or at least one salt of an acidic group having a pKa of less than 11, or a mixture of at least one acidic group having a pKa of less than 11 and at least one salt of an acidic group having a pKa of less than 11. The pKa of the acidic group refers to the pKa of the organic group as a whole, not just the acidic substituent. More preferably, the pKa is less than 10 and most preferably less than 9. Preferably, the aromatic group or the alkyl group of the organic group is directly attached to the carbon product. The aromatic group may be further substituted or unsubstituted, for example, with alkyl groups. The $C_1$–$C_{12}$ alkyl group may be branched or unbranched and is preferably ethyl. More preferably, the organic group is a phenyl or a naphthyl group and the acidic group is a sulfonic acid group, a sulfinic acid group, a phosphonic acid group, or a carboxylic acid group. Examples include —COOH, —$SO_3H$ and —$PO_3H_2$, —$SO_2NH_2$, —$SO_2NHCOR$, and their salts, for example —COONa, —COOK, —$COO^-NR_4^+$, —$SO_3Na$, —$HPO_3Na$, —$SO_3^-N_4^+$, and $PO_3Na_2$, where R is an alkyl or phenyl group. Particularly preferred ionizable substituents are —COOH and —$SO_3H$ and their sodium, potassium, lithium salts. It is understood these cationic counter ions can be exchanged to other ions through an ion-exchange process.

Most preferably, the organic group is a substituted or unsubstituted sulfophenyl group or a salt thereof; a substituted or unsubstituted (polysulfo)phenyl group or a salt thereof; a substituted or unsubstituted sulfonaphthyl group or a salt thereof; or a substituted or unsubstituted (polysulfo) naphthyl group or a salt thereof A preferred substituted sulfophenyl group is hydroxysulfophenyl group or a salt thereof. Specific organic groups having an ionizable functional group forming an anion are p-sulfophenyl, 4-hydroxy-3-sulfophenyl, and 2-sulfoethyl. More preferred examples include p-$C_6H_4SO_3^-Na^+$ and $C_6H_4CO_2^-Na^+$.

Amines represent examples of ionizable functional groups that form cationic groups and can be attached to the same organic groups as discussed above for the ionizable groups which form anions. For example, amines may be protonated to form ammonium groups in acidic media. Preferably, an organic group having an amine substituent has a pKb of less than 5. Quaternary ammonium groups (—$NR_3^+$), quaternary phosphonium groups (—$PR_3^+$), and sulfonium groups (—$SR_2^+$) also represent examples of cationic groups and can be attached to the same organic groups as discussed above for the ionizable groups which form anions. Preferably, the organic group contains an aromatic group such as a phenyl or a naphthyl group and a quaternary ammonium, a quaternary phosphonium group, or a sulfonium group. The aromatic group is preferably directly attached to the carbon product. Quaternized cyclic amines and quaternized aromatic amines can also be used as the organic group. Thus, N-substituted pyridinium compounds, such as N-methyl-pyridyl, can be used in this regard. Examples of organic groups include, but are not limited to, 3-$C_5H_4N(C_2H_5)^+$, $C_6H_4NC_5H_5^+$, $C_6H_4COCH_2N(CH_3)_3^+$, $C_6H_4COCH_2(NC_5H_5)^+$, 3-$C_5H_4N(CH_3)^+$, and $C_6H_4CH_2N(CH_3)_3^+$. Counter ions to those groups include, but are not limited to, $Cl^-$, $NO_3^-$, $OH^-$, and $CH_3COO^-$. It is understood that these anionic counter ions can be exchanged to other ions through an ion-exchange process.

As stated earlier, non-ionic hydrophilic groups can be used. Examples of the non-ionic hydrophilic groups include, but are not limited to, groups having no apparent ionic change and can not be transformed to have an ionic charge, such as polymers/oligomers of the ethylene oxide, propylene oxide, other alkylene oxides, glycols, alcohols, and the like.

As part of the present invention, it is preferred that the amount of hydrophilic organic groups attached to the carbon product is controlled in order to avoid making the modified carbon product overly hydrophilic. In particular, as a preferred embodiment of the preferred invention, the treatment level, which is expressed in terms of $\mu mol/m^2$ of carbon, of the hydrophilic organic group on the carbon product is from about 0.04 $\mu mol/m^2$ to about 6 $\mu mol/m^2$, more preferably from about 0.1 $\mu mol/m^2$ to about 2 $\mu mol/m^2$, and most preferably from about 0.2 $\mu mol/m^2$ to about 0.8 $\mu mol/m^2$.

In a more preferred embodiment of the present invention, the carbon product which has attached at least one hydrophilic organic group, also has attached at least one hydrophobic organic group as well to better promote a hydrophobic/hydrophilic balance in the active layer. The hydrophobic organic groups can be the same as described above. For purposes of this preferred embodiment of the present invention, the treatment level of the hydrophobic organic group on the modified carbon product is preferably from about 0.04 $\mu mol/m^2$ to about 6 $\mu mol/m^2$, more preferably from about 0.1 $\mu mol/m^2$ to about 4 $mol/m^2$, and most preferably from about 0.5 $\mu mol/m^2$ to about 3 $\mu mol/m^2$.

Alternatively, instead of a dual or multi-treated modified carbon product as described above in the preferred embodiment, two or more different types of modified carbon products can be used, in particular, one modified carbon product can be a carbon product having attached at least one hydrophilic organic group and a second type of modified carbon product can be used which is a carbon product having attached at least one hydrophobic organic group. Then, in this embodiment, a mixture of the two different types of modified carbon products can be used to form the active layer along with the presence of a binder.

Any carbon products that are used in air-diffusion electrodes can be used in the present invention. Examples of such carbon products include, but are not limited to, graphite, carbon black, vitreous carbon, activated charcoal, carbon fiber, activated carbon, and carbon aerogel. Catalyzed carbon products that are used in air-diffusion electrodes can also be used in the present invention, wherein surface modification can be performed either before or after the catalization step. Finely divided forms of the above are preferred. Further, mixtures of different carbon products can be used. Preferably, the carbon product used is capable of reacting with a diazonium salt to form the above-mentioned carbon products. The carbon may be of the crystalline or amorphous type. In addition, mixtures of different types of modified carbon products with or without unmodified carbon products can also be used in the present invention as one embodiment.

The organic groups which are attached onto the carbon product to form a modified carbon product can be attached by the methods described in the following U.S. Patents and Publications which are all incorporated in their entirety by reference herein: U.S. Pat. Nos. 5,851,280; 5,837,045; 5,803,959; 5,672,198; 5,571,311; 5,630,868; 5,707,432; 5,803,959; 5,554,739; 5,689,016; 5,713,988; WO 96/18688; WO 97/47697; and WO 97/47699.

Besides the presence of the modified carbon product in one or more components of the electrode described above, conventional ingredients used in electrodes can also be present in the electrodes of the present invention. For instance, fluorine containing compounds typically used in air-diffusion electrodes can also be used in the present invention such as polytetrafluoroethylene in the blocking layer. Likewise, in the active layer, a perfluoric sulphonic acid polymer sold under the trade name Nafion® can be used with the modified carbon products. However, one preferred advantage of the present invention is the ability to reduce such fluorine containing compounds in the blocking layer and/or active layer. The proper choice of organic groups attached onto the carbon product to form the modified carbon product can lead to a decrease if not an elimination of fluorine containing compounds which in the past have been used in conjunction with carbon black in order to promote the hydrophilic and/or hydrophobic properties discussed above. The reduction or elimination of such fluorine containing compounds can greatly reduce the cost of the electrodes and thus the present invention provides a very economical electrode. Preferably, for purposes of the present invention, the amount of the reduction of a hydrophobic fluorine containing compound in the blocking layer is from about 10 to about 100% by weight, more preferably from about 40 to about 100% by weight. Further, with respect to the active layer, preferably the amount of reduction of the fluorine containing compound is from about 10 to about 100% by weight, more preferably from about 60 to about 100% by weight.

The electrodes containing the modified carbon products of the present invention also permit the extension of the service life of the electrode. Generally, at least two processes could negatively influence the performance of the gas diffusion electrode during its long time operation as an oxygen reduction cathode: oxidation of the carbon surface due to the decomposition of the hydroperoxide anion $HO_2^-$ which is an intermediate product of the oxygen reduction; and the excessive wetting of the internal microporous structure. It is well known experimentally that the second of the above processes predominates in the electrode performance failure during long time operation.

Gas diffusion electrodes are fabricated so as to produce the maximum area of a three-phase interface, that is the maximum area of contact between the electrolyte, the gaseous reactant and the catalyst supported on carbon as the electronically conducting material. As discussed before, the partially wet-proofed catalyst layer is currently achieved by the mixture of the catalysed carbon particles with a hydrophilic agent. The additional use of PTFE was considered necessary so that the catalyst would not flood from the presence of liquid electrolyte. The net result is a structure in which the PTFE selectively wets parts of the catalyst agglomerates on a rather random basis. The areas where the carbon carrying the catalyst has become wetted by PTFE are hydrophobic, producing the gas pores, whereas those areas not covered by a PTFE film become the hydrophilic electrolyte pores. The long-term stability of the three-phase interface in hydrophobic porous Teflon-bonded carbon electrodes is difficult to achieve. PTFE doesn't dissolve in any known solvent and consequently the conventional process of fabricating an electrode is complicated by the use of a liquid suspension. In particular, when the electrodes are made in this fashion, it is quite difficult to control the electrode structure and the porosity.

Moreover catalyst utilization has been rather poor because of the nature of the interface. It was found that, in conventional electrodes, a large part of the catalyst is not effective. The electrochemical reaction takes place only in those areas where catalyst is accessible both to the reactant gas and the electrolyte. PTFE makes the catalytic layer partly impermeable to the electrolyte so that the catalyst efficiency is lowered, also resulting in the decrease of the electrode performance. On the other hand, a large amount of PTFE is required in the gas diffusion layer to prevent the electrolyte diffusivity over a long period of time. This results in the reduction of the gas mass transport efficiency due to the blocking effect of PTFE inside the fine porous structure.

Since the modified carbon products of the present invention promote hydrophobic and/or hydrophilic properties on a molecular scale, there is no random wetting of the carbon products and a very even distribution of the wetting characteristics exists throughout the active layer for instance. Thus, the unwanted excessive wetting of the carbon products can be avoided throughout the entire active layer which then leads to a long term operation thus promoting the extension of the service life of the electrode. Further, with respect to the blocking layer, with a modified carbon product having attached hydrophobic organic groups, the blocking layer quite effectively blocks any electrolyte and permits the greatest amount of air diffusion.

Besides air electrodes, the present invention relates to gas diffusion electrodes in general, wherein the active layer and/or blocking layer that may be present in gas-diffusion electrodes can include modified carbon products as described above and serve the same function as the modified carbon products incorporated in the active layer and/or blocking layer of the electrode. Gas-diffusion electrodes, which include air-diffusion electrodes, prepared with modified carbon material have broad applications. One example of a gas diffusion electrode application would be a phosphoric acid type fuel-cell using a pair of gas diffusion electrodes. Such gas diffusion electrodes are described, for instance, in U.S. Pat. Nos. 5,846,670; 5,232,561; and 5,116, 592, all incorporated in their entirety by reference herein. Other applications are described in EP 435835, (Electroplating); U.S. Pat. Nos. 5,783,325; 5,561,000; 5,521,020 (Solid polymer electrolyte fuel cells); U.S. Pat. No. 5,733, 430 (Sodium chloride electorlysis); U.S. Pat. No. 5,531,883 (Ozone generation cells); U.S. Pat. No. 5,302,274 (Gas Sensor); U.S. Pat. No. 4,892,637 (Alkali chloride electrolyzers, air cells, and fuel cells); EP 327 018 A2 (Biosensors); A. Kaishera et al., Sens. Actuators, 1995, 1327 ((1–3) (Biosensors), all are incorporated herein in their entirety by reference.

The present invention can be used in a variety of gas diffusion electrodes. For instance, but without limiting the present invention, the present invention can be used in large scale industrial applications, such as chemical production. Examples of such industrial applications include, but are not limited to, chloro-alkali production (e.g., the production of sodium hydroxide also known as salt splitting and chlorine production), hydrogen peroxide production; and the like. The present invention can also be used, as discussed above, in fuel cells, metal/air batteries, electro-platting (e.g., using hydrogen gas); ozone production, carbon dioxide decomposition; sensors for such chemicals as ozone, oxygen, nitrogen dioxide, and the like; enzyme/gas diffusion electrodes (e.g., biosensors); and the like. Each of these applications can incorporate the modified carbon material of the present invention in the electrode to obtain the benefits discussed above and one skilled in the art in view of the disclosure set forth in this present invention can apply this present invention to these various applications and therefore are considered part of the present application.

The following examples further illustrate aspects of the present invention but do not limit the present invention.

EXAMPLES

Example 1

0.5 mmol/g Treatment with 3-trifluoromethyl Aniline

Preparation of a Hydrophobic Carbon Black Product with Diazonium Salt

This example illustrates the preparation of a hydrophobic carbon black product of the present invention. A fluffy VXC-72R carbon black with a surface area of 254 $m^2/g$ and a DBPA of 192 cc/100 g was used. Forty grams of the fluffy carbon black were added to a solution of 3.22 g of 3-trifluoromethyl aniline dissolved in 900 g of de-ionized water and 1.8 g of 70% nitric acid at 70° C. Then 100 mL of iso-propanol was added to assist the wetting of carbon black. To the reaction solution, 1.38 g of sodium nitrite dissolved in 30 g of deionized water was added drop by drop over a period of several minutes and stirred rapidly, to produce a diazonium salt, which reacted with the carbon black. The resulting reaction mixture was stirred rapidly for two more hours before cooled back to room temperature. Surface modified carbon black product was then filtered out by vacuum filtration. The crude modified carbon black was dried at 70° C. overnight. The carbon black product contained 1.36% of fluorine (equivalent to 0.24 mmol/g of surface 3-trifluoromethyl-phenyl attachment to carbon black) after Soxhlet extraction with methanol overnight.

Example 2

0.25 mmol/g Treatment with 3-trifluoromethyl Aniline

Preparation of a Hydrophobic Carbon Black Product with Diazonium Salt

Modified carbon black product of this example was prepared following the procedure described in Example 1; except, 1.61 g of 3-trifluoromethyl aniline, 0.9 g of nitric acid, and 0.69 g of sodium nitrite were used. The carbon black product contained 0.68% of fluorine (equivalent to 0.12 mmol/g of surface 3-trifluoromethyl-phenyl attachment to carbon black) after Soxhlet extraction with methanol overnight.

Example 3

0.1 mmol/g Treatment with 3-trifluoromethyl Aniline

Preparation of a Hydrophobic Carbon Black Product with Diazonium Salt

Modified carbon black product of this example was prepared following the procedure described in Example 1; except, 0.64 g of 3-trifluoromethyl aniline, 0.36 g of nitric acid, and 0.28 g of sodium nitrite were used. The carbon black product contained 0.30% of fluorine (equivalent to 0.05 mmol/g of surface 3-trifluoromethyl-phenyl attachment to carbon black) after Soxhlet extraction with methanol overnight.

Example 4

0.1 mmol/g, Sulfanilic Acid

Preparation of a Hydrophilic Carbon Black Product with Diazonium Salt

This example illustrates the preparation of a hydrophilic carbon black product of the present invention. A fluffy VXC-72R carbon black with a surface area of 254 $m^2/g$ and a DBPA of 192 cc/100 g was used. Forty grams of the fluffy carbon black were added to a solution of 0.70 g of sulfanilic acid dissolved in 480 g of de-ionized water at 70° C. To that reaction solution, 0.28 g of sodium nitrite dissolved in 20 g of de-ionized water was added drop by drop over a period of several minutes and stirred rapidly, to produce a diazonium salt, which reacted with the carbon black. The resulting reaction mixture was stirred rapidly for two more hours before cooled back to room temperature. The reaction mixture was poured into a drying dish and dried at 70° C. for 2 days. The carbon black product contained 0.8% of sulfur (There was 0.5% sulfur on the starting VXC-72R, so that 0.3% of sulfur were introduced by the surface modification reaction which was equivalent to 0.09 mmol/g of surface attachment to carbon black) after Soxhlet extraction with toluene overnight and then methanol overnight.

Example 5

0.1 mol/g of Sulfanilic Acid 0.2 mmol/g 3-trifluoromethyl Aniline

Preparation of a Hydrophobic/Hydrophilic Carbon Black Product with Diazonium Salt Dual Treatment This example illustrates the preparation of a hydrophobic/hydrophilic carbon black product of the present invention. A fluffy VXC-72R carbon black with a surface area of 254 $m^2/g$ and a DBPA of 192 cc/100 g was used. Forty grams of the fluffy carbon black were added to a solution of 0.70 g of sulfanilic acid dissolved in 480 g of de-ionized water and 20 g of iso-propanol at 70° C. To that reaction solution, 0.28 g of sodium nitrite dissolved in 20 g of deionized water was added drop by drop over a period of several minutes and stirred rapidly, to produce a diazonium salt, which reacted with the carbon black. The resulting reaction mixture was stirred rapidly for two hours before an additional 220 g of de-ionized water and 30 g of iso-propanol were added. Then, 1.3 g of 3-trifluoromethyl aniline and 0.52 g of 70% nitric acid were added. To that reaction solution, 0.56 g of sodium nitrite dissolved in 20 g of de-ionized water was added drop by drop over a period of several minutes and stirred rapidly, to produce a second diazonium salt, which reacted with the carbon black. The resulting reaction mixture was stirred rapidly for two more hours before cooled back to room temperature. The reaction mixture was poured into a drying dish and dried at 70° C. for 2 days. The carbon black product contained 0.83% of sulfur (There was 0.5% sulfur on the starting VXC-72R, so that 0.33% of sulfur were introduced by the surface modification reaction which was equivalent to 0.1 mmol/g of surface attachment to carbon black.), and 0.67% of fluorine (equivalent to 0.11 mmol/g of surface hydrophobic treatment to carbon black) after Soxhlet extraction with toluene overnight and then methanol overnight.

Example 6

PTFE, FEP Treatment

Preparation of a Fluoro-polymer Bonded Carbon Black Product

Twenty grams of carbon black material prepared in Example 1 were made into fluffy form by chopping the carbon black in an industrial blender for 3 minutes. Those carbon black were then added to a beaker with 730 g of de-ionized water and 40 mL of iso-propanol at 80° C. The carbon black suspension was stirred rapidly for 90 minutes before 5.55 g of DuPont Teflon 30 (polytetrafluoroethylene, PTFE water dispersion), and 17.92 g of DuPont Teflon 121A (fluorinated ethylene propylene co-polymer FEP-water dispersion) were added. An additional 300 g of de-ionized water was added and the mixture was stirred for additional 2 hours at 80° C. After cooling the mixture to room temperature the fluoro polymer bonded carbon black product was isolated by vacuum filtration. The carbon material was then dried at 150° C. overnight followed by 310° C. overnight.

Example 7

Example 2, with PTFE, FEP Treatment

Preparation of a Fluoro-polymer Bonded Carbon Black Product

Fluoro-polymer bonded carbon material of this example was prepared according to the procedure in Example 6, except the starting carbon black material used was prepared in Example 2.

Example 8

Example 3, with PTFE FEP Treatment

Preparation of a Fluoro-polymer Bonded Carbon Black Product

Fluoro-polymer bonded carbon material of this example was prepared according to the procedure in Example 6, except the starting carbon black material used was prepared in Example 3.

Example 9

Example 1, with FEP Treatment

Preparation of a Fluoro-polymer Bonded Carbon Black Product

Fifteen grams of carbon black material prepared in Example 1 were made into fluffy form by chopping the product in an industrial blender for 3 minutes. The carbon black were then added to a beaker with 550 g of de-ionized water and 30 mL of iso-propanol at 80° C. The carbon black suspension was stirred rapidly for 60 minutes before 13.44 g of DuPont Teflon 121A were added. Additional 200 g of de-ionized water was added and the mixture was stirred for additional 2 hours at 80° C. After cooling the mixture to room temperature the fluoro polymer bonded carbon black product was isolated by vacuum filtration. The carbon material was then dried at 150° C. overnight and followed by 310° C. overnight.

Example 10

Example 2, with FEP Treatment

Preparation of a Fluoro-polymer Bonded Carbon Black Product

Fluoro-polymer bonded carbon material of this example was prepared according to the procedure in Example 9, except the starting carbon black material used was prepared in Example 2.

Example 11

Example 3, with FEP Treatment

Preparation of a Fluoro-polymer Bonded Carbon Black Product

Fluoro-polymer bonded carbon material of this example was prepared according to the procedure in Example 9, except the starting carbon black material used was prepared in Example 3.

Example 12

Preparation of an Active Layer Material

For the preparation of the active layer powder, the modified carbon product of Example 5 was combined with isopropyl alcohol to form a mixture having a paste-like consistency.

Example 13

Preparation of an Active Layer Material

In this Example, the modified carbon product of Example 5 was mixed with a commercially available fluorinated ethylene propylene copolymer powder ( FEP 5328000, Du Pont) in a ratio of about 2 part by weight carbon and 1 part by weight FEP. The polymer serves as a binder for the carbon black particles to ensure the physical integrity of the electrode structure and its mechanical strength.

The above carbon/FEP mixture was mechanically blended and grinded for several minutes and then the resulting active layer powder was added to isopropanol to form a material having a paste-like consistency.

Example 14

Preparation of an Active Layer Material

In this example, the modified carbon product of Example 5 was made more hydrophobic by impregnation in a FEP solution. The modified carbon product was first stirred in distilled water using 50 mls of water per gram of carbon black.

A separate aqueous dispersion was prepared by diluting commercially available ethylene propylene co-polymer dispersion ( FEP 120-N, Du Pont) with distilled water using 18 mls of water per ml of said dispersion. Then the diluted FEP emulsion was added to the modified carbon slurry to make a mixture containing 2 part by weight carbon and 1 part by weight FEP. The mixture was stirred for 90 min at 85° C. and then filtered through a fine pore membrane. The resulting carbon/FEP paste was dried in an oven at 110° C. to remove solvent (water and isopropyl alcohol). Finally the mixture was dried at a temperature that ranged from 260 to 310° C. for 24 h to remove the residual surfactant agents.

The product was then micronized to a fine powder and blended in isopropanol to obtain a dispersion to be used as active layer material. The amount used was 40 mls of solvent per g of modified carbon product.

Example 15

Preparation of a Catalyzed Active Layer Material

A somewhat different process was required for the preparation of a catalysed active layer. The catalytic material was a macrocycled chelate compound, which was a cobalt porphyrin. The addition of the cobalt porphyrin to carbon was achieved by intimately mixing the modified carbon product and catalyst, followed by heat treatment in furnace under a continuous flow of inert gas. The carbon-supported catalyst was heated to high temperature (900° C. for 1 h) in order to be activated. The electrocatalytic activity of cobalt-containing macrocyclics significantly improved after heating the carbon-supported material to high temperatures.

After such pyrolisis, the pyrolyzed mixture was finely grounded. From this point on the aforementioned carbon product was made hydrophilic following the procedure described in Example 4 or, otherwise, it was made partially hydrophobic and partly hydrophilic following the procedure described in Example 5. Finally the catalyzed active layer powder was prepared beginning from the catalyzed and modified carbon particles described above and carrying out the procedure of Example 12 or 13 or 14.

Example 16

For comparison purposes, three separate double-layer air electrodes were fabricated:

i) Electrode A was prepared from carbon powder modified as described above.

First, 6 g of active paste prepared as described in Example 13 were spread over a nickel mesh to integrate the current collector into a composite structure supported on a separable filter paper. This structure was then air dried. Subsequently, 8 g of blocking powder in the alcoholic dispersion as described in Example 1 were filtered on the above-prepared active layer which provided a freshly deposited diffusion layer. The resulting double-layer electrode was pressed at 120° C. and 30 tons to form a sheet ranging in thickness from 0.50 to 0.58 mm. Finally the dried electrode was sintered at a temperature between 280° C. and 300° C. at moderate pressure.

ii) Electrode B was produced by following the conventional techniques of the state-of-the-art, specifically electrode B was produced according to the standard procedure described in the U.S. Pat. No. 5,441,823 (Electric Fuel Ltd) and U.S. Pat. No. 4,927,514 (Eltech Systems Co.), incorporated in their entirety herein by reference. This electrode was prepared from untreated Vulcan XC-72R carbon black.

The powder for use in preparing the active layer was prepared by dispersing 7.5 weight parts of carbon and 2.5 weight parts of Nafion® (5% solution) together with isopropanol. The mixture was evaporated to dryness with constant stirring at 65° C. and then the solid was further dried under vacuum at 110° C., overnight. The product was finely ground and blended with FEP powder at a ratio of 2:1 by weight. The powder for use in preparing a diffusion layer was provided by dispersing carbon in distilled water at 85° C. by means of an overhead stirrer. To this there were added dispersions of PTFE and FEP sufficient to provide a weight ratio of PTFE to FEP to carbon of 1:3:6. The mixture was further blended by stirring and then filtered through a fine pore membrane. The moist solid was dried overnight in an oven at 150° C. and then heat treated at 310° C. for 12 h. Finally the product was ground. A hydrophilic active layer was then prepared by first mixing 6.0 g of the nafionized carbon/FEP fine powder with few drops of isopropanol alcohol and then depositing the resulting paste on a separable filter paper onto which a nickel mesh current collector was placed. A mixture of the finely blocking material (8.0 g) was added to isopropanol and homogenised in a blender. The resulting dispersion was then filtered on the above-prepared active layer which provided a freshly deposited blocking layer having a mud-like consistency. The filter paper was removed and the resulting matrix was dried at 120° C. while being compressed. The dried matrix was sintered at 285° C. under a moderate pressure.

iii) Electrode C was prepared in the same manner as electrode B, except for using Shawinigan black (Chevron Chemical Company) instead of Vulcan XC-72R.

ELECTROCHEMICAL MEASUREMENTS

The activity of electrodes for the reduction of oxygen was determined using a conventional half-cell arrangement.

The air electrode was located on one of the walls of the container and it was held between a holder and a stainless steel end plate acting as a current collector. The test electrode was mounted having the active layer faced towards the electrolyte. The reactant gas (air or oxygen) was fed at a constant flow rate of 12 nl/h from the rear. The reactant gas was introduced into the holder from a side hole and released from a second hole. The electrolyte consisted of 7.5 M KOH and was stirred throughout the experiment. The potential of the working electrode was recorded against an Hg/HgO, KOH reference electrode. All potentials are reported with regard to this electrode. A nickel plate served as counter electrode.

Electrochemical measurements were taken using a programmable power supply which was interfaced with a personal computer for programming, data acquisition, plotting, and analysis.

The electrodes were tested galvanostatically for the evaluation of performance comparisons. A constant current density of 200 mA/cm$^2$ was applied in the life test of the electrodes. After set periods of operation the tests were temporarily interrupted to obtain the steady-state current/potential curves. The test was performed by passing a current between the air electrode and the counter electrode, and measuring the resulting voltage drop between the air electrode and the reference electrode. The current was increased stepwise every 60 sec and the potential was logged in the steady state. All of the denoted polarization curves contained IR resistance. The electrodes were kept in contact with KOH 7.5 M for 24 h to achieve a complete soakage.

FIG. 1 shows the potential-time curves under a current load of 200 mA/cm$^2$ and 23° C. for the electrodes prepared.

The electrodes showed a potential change during the so-called break-in-time, The load potential starts more negative and gradually increases to more positive levels which can be 0.1 V or more higher than the initial values when stabilised. The phenomenon was attributed to a wetting process in the active layer where the electrolyte slowly reaches a maximum contact area with the catalytic sites.

It can be seen that the performance of the untreated carbon-based electrodes (Electrode B and C) deteriorated rapidly after a service of few hours. The decrease of activity can be explained by a reduction of surface area available at the electrochemical reaction. A progressive flooding of the electrodes by the liquid electrolyte hindered the regular flow of reagent gases through the porous structure.

It was evident that the performance of the modified carbon-based electrode (Electrode A) was superior to those obtained with untreated carbon (Electrode B and C). The long term stability of Electrode A and C have been tested. In FIG. 2 it can be seen that the degradation of the Electrode C was high during the first 100 h, after which the electrode became stable. Viceversa it is found that the Electrode A has so far been stable without appreciable deterioration for more than 500 h.

The polarisation curve of modified carbon-based electrode (Electrode A) which operated as oxygen reduction cathode is presented in FIG. 3. The same figure also presents the curves for the electrodes prepared with untreated Shawinigan-based carbon (Electrode C). These polarization curves were recorded after 50 h of electrode operation in an oxygen reduction mode at 200 mA/cm$^2$. In earlier experiments, it was found that this procedure resulted in stabilization of the electrode performance.

The results show that the modified carbon-based electrode have better performance than conventional electrodes. The conventional electrodes have a higher ohmic resistance which was indicated by the higher slope of the polarization curves. The maximum activity of the modified carbon-based electrode overpassed the one obtained with untreated Shawinigan carbon-based electrode. Polarisation curves in FIG. 3 indicated that Electrode A can sustain a load currentdensity of 200 mA/cm$^2$ with a polarisation of about −395 mV vs Hg/HgO. By contrast, higher polarisation values are observed for the Electrode B. A gain of almost 320 mV at 200 mA/cm$^2$ for the electrode with modified carbon products was observed. These results demonstrated the benefits of preparing carbon supports in which carbon is modified with functional groups on its surface.

Chemically treated carbon supports are much suitable from the hydrophobic point of view and a long life of the gas diffusion electrodes can be secured without the deterioration of the performance due to the permeation of the electrolyte into the gas feed channels.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A modified carbon product comprising a carbon product having attached at least one hydrophobic organic group and at least one hydrophilic organic group.

2. The modified carbon product of claim 1, wherein said carbon product is carbon black.

3. The modified carbon product claim 1, wherein said carbon product is graphite, carbon black, vitreous carbon, activated charcoal, carbon aerogel, carbon fiber, activated carbon, or mixtures thereof.

4. The modified carbon product of claim 1, wherein said hydrophobic organic group comprises at least one aromatic group or a $C_1$–$C_{20}$ alkyl group.

5. The modified carbon product of claim 1, wherein said hydrophilic organic group comprises at least one aromatic group or at least one alkyl group and b) at least one ionic group, at least one ionizable group, or a mixture of an ionic group and an ionizable group.

6. The modified carbon product of claim 4, wherein said at least one aromatic group or at least one $C_1$–$C_{12}$ alkyl group is directly attached to the carbon product.

7. The modified carbon product of claim 5, wherein the ionic or the ionizable group comprises a carboxylic acid, a sulfonic acid, a quaternary ammonium salt, a phosphonium, a sulfonium, a sulfonylamide group, or salts thereof.

8. The modified carbon product of claim 1, wherein the hydrophilic organic group is a sulfophenyl group, a carboxyphenyl group, or salts thereof.

9. The modified carbon product of claim 1, wherein said hydrophilic organic group is p-$C_6H_4SO_3^-Na^+$ or $C_6H_4CO_2^-Na^+$.

10. The modified carbon product of claim 1, wherein said hydrophobic organic group is a fluorine-containing group.

11. The modified carbon product of claim 1, wherein said hydrophobic organic group has the formula —Ar—$CF_3$.

12. The modified carbon product of claim 1, wherein said organic group has the formula —A—R, where A is an alkyl group or an aromatic group and R is a fluorine containing substituent.

13. The modified carbon product of claim 1, wherein said hydrophilic organic group is a non-ionic hydrophilic group.

14. The modified carbon product of claim 13, wherein said non-ionic hydrophilic group is a polymer or oligomer of an alkylene oxide, glycol, or alcohol.

15. The modified carbon product of claim 1, wherein said hydrophobic organic is present at a treatment level of from about 0.04 $\mu$mol/m$^2$ of carbon to about 6 $\mu$mol/m$^2$ of carbon and said hydrophilic organic group is present at a treatment level of from about 0.04 $\mu$mol/m$^2$ of carbon to about 6 $\mu$mol/m$^2$ of carbon.

16. The modified carbon product of claim 1, wherein said hydrophobic organic is present at a treatment level of from about 0.1 $\mu$mol/m$^2$ of carbon to about 4 $\mu$mol/m$^2$ of carbon and said hydrophilic organic group is present at a treatment level of from about 0.1 $\mu$mol/m$^2$ of carbon to about 2 $\mu$mol/m$^2$ of carbon.

17. The modified carbon product of claim 1, wherein said hydrophobic organic is present at a treatment level of from about 0.5 $\mu$mol/m$^2$ of carbon to about 3 $\mu$mol/m$^2$ of carbon and said hydrophilic organic group is present at a treatment level of from about 0.2 $\mu$mol/m$^2$ of carbon to about 0.8 $\mu$mol/m$^2$ of carbon.

18. The modified carbon product of claim 1, wherein said at least one hydrophilic organic group is a sulfophenyl group or a carboxyphenyl group or salts thereof and said at least one hydrophobic organic group is a per-fluoro alkyl substituted phenyl group.

19. The modified carbon product of claim 1, wherein said at least one hydrophilic organic group is a sulfophenyl group or salt thereof and said at least one hydrophobic organic group is a meta tri-fluoromethyl substituted phenyl group.

* * * * *